United States Patent [19]

Boner et al.

[11] Patent Number: 4,681,103
[45] Date of Patent: Jul. 21, 1987

[54] ULTRASOUND GUIDED SURGICAL INSTRUMENT GUIDE AND METHOD

[75] Inventors: James C. Boner, Los Gatos; Mitchel S. Berger, San Francisco; Marc Fine, Santa Rosa, all of Calif.

[73] Assignee: Diasonics, Inc., Milpitas, Calif.

[21] Appl. No.: 710,068

[22] Filed: Mar. 11, 1985

[51] Int. Cl.⁴ .............................................. A61B 8/12
[52] U.S. Cl. .............................. 128/303 B; 128/660; 128/754
[58] Field of Search ................... 128/303 B, 751, 752, 128/753, 754, 660, 24 A

[56] References Cited

U.S. PATENT DOCUMENTS

| | | | |
|---|---|---|---|
| 3,017,887 | 1/1962 | Heyer | 128/303 B X |
| 3,021,842 | 2/1962 | Flood | 128/303 B |
| 3,135,263 | 6/1964 | Connelley, Jr. | 128/303 B |
| 3,457,922 | 7/1969 | Ray | 128/303 B |
| 4,058,114 | 11/1977 | Soldner | 128/754 X |
| 4,108,165 | 8/1978 | Kopp et al. | 128/660 |
| 4,346,717 | 8/1982 | Haerten | 128/660 |
| 4,483,344 | 11/1984 | Atkov et al. | 128/303 B X |

FOREIGN PATENT DOCUMENTS

| | | | |
|---|---|---|---|
| 0025214 | 3/1981 | European Pat. Off. | 128/303 B |
| 2942405 | 4/1981 | Fed. Rep. of Germany | 128/660 |

OTHER PUBLICATIONS

Goldberg, B. B. and Pollack, H. M., "Ultrasound Aspiration Biopsy Techniques", Journal of Clinical Ultrasound vol. 4, #2, 4/1976 pp. 141-151.

Primary Examiner—William R. Cline
Assistant Examiner—Randolph A. Smith
Attorney, Agent, or Firm—Blakely, Sokoloff Taylor & Zafman

[57] ABSTRACT

A surgical instrument guide for use in conjunction with an ultrasound probe and the method of use is described. The guide comprises an ultrasound probe socket disposed in a housing so that it can pivot or be locked in place with respect to the housing. An instrument holder adapted to fit in the probe socket and hold a surgical instrument along its longitudinal axis is also provided. The housing has external threads on the bottom thereof to enable the device to be screwed into the skull.

4 Claims, 10 Drawing Figures

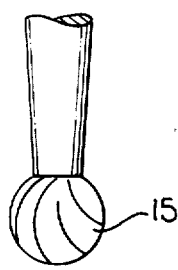
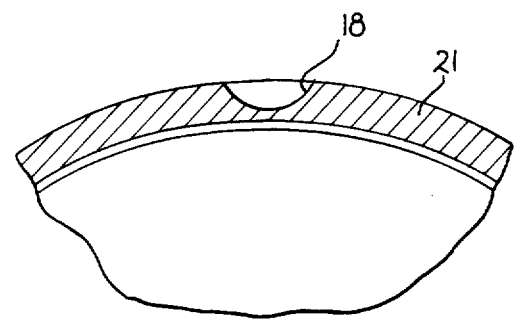
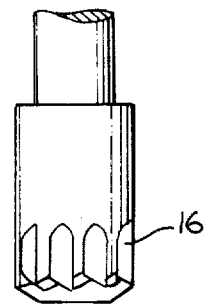
Fig.1  Fig.2
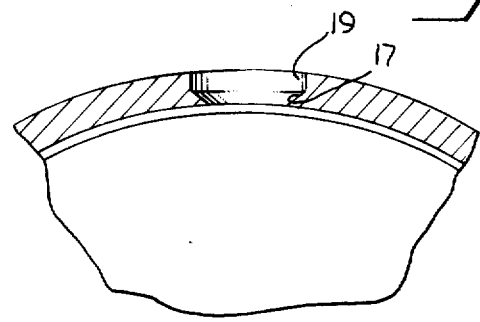
Fig.3

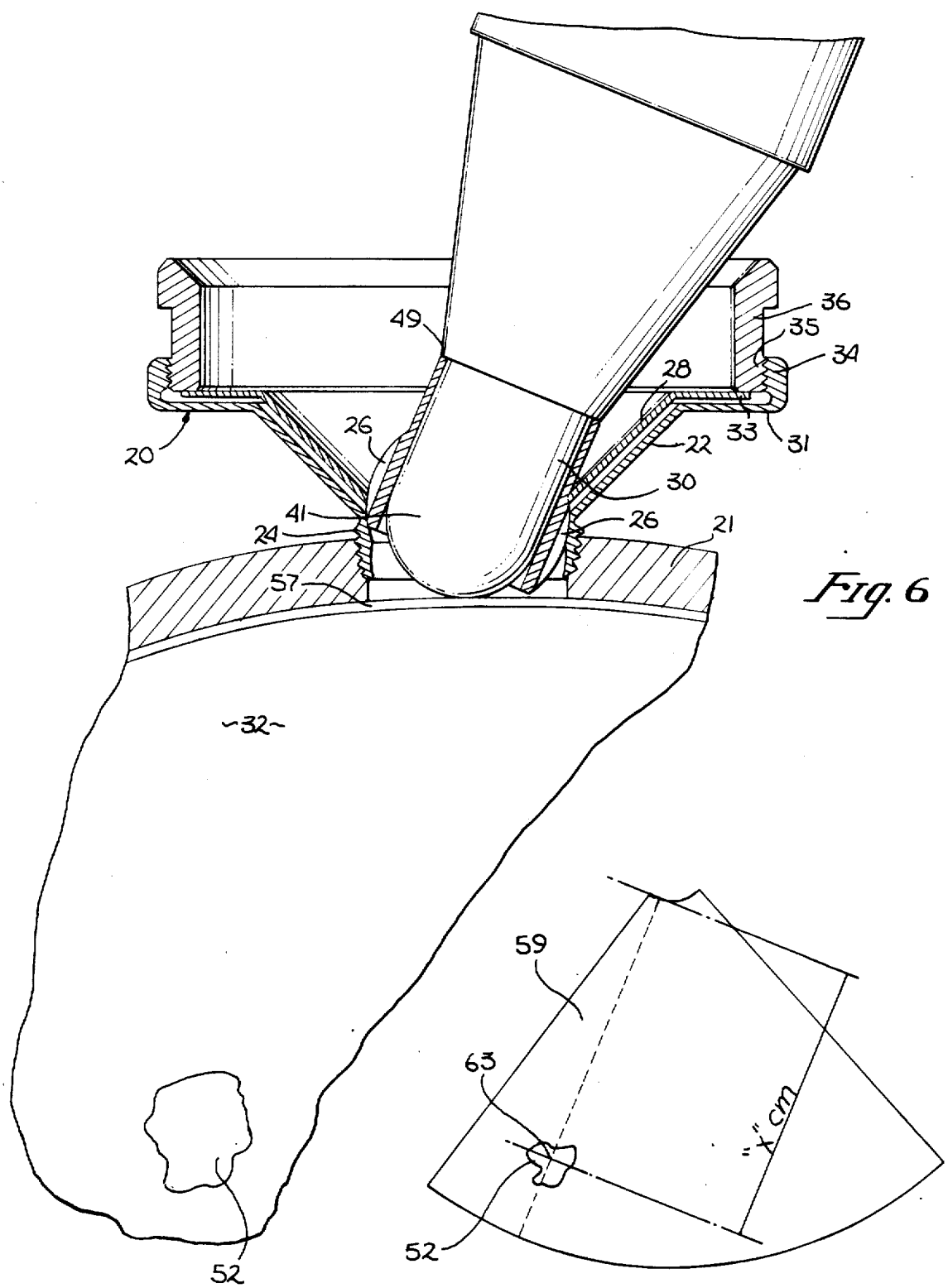

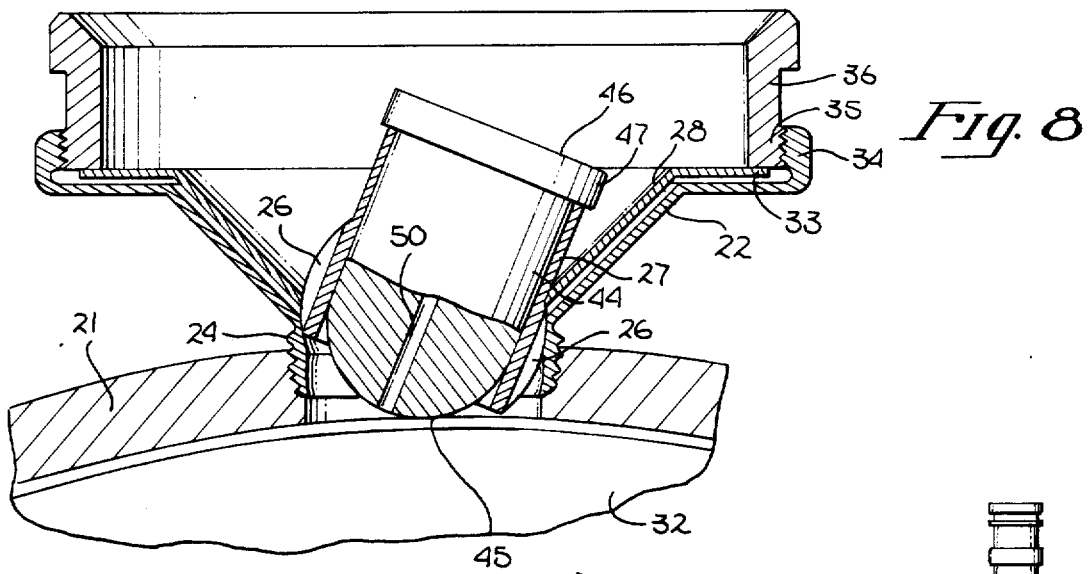
Fig. 8
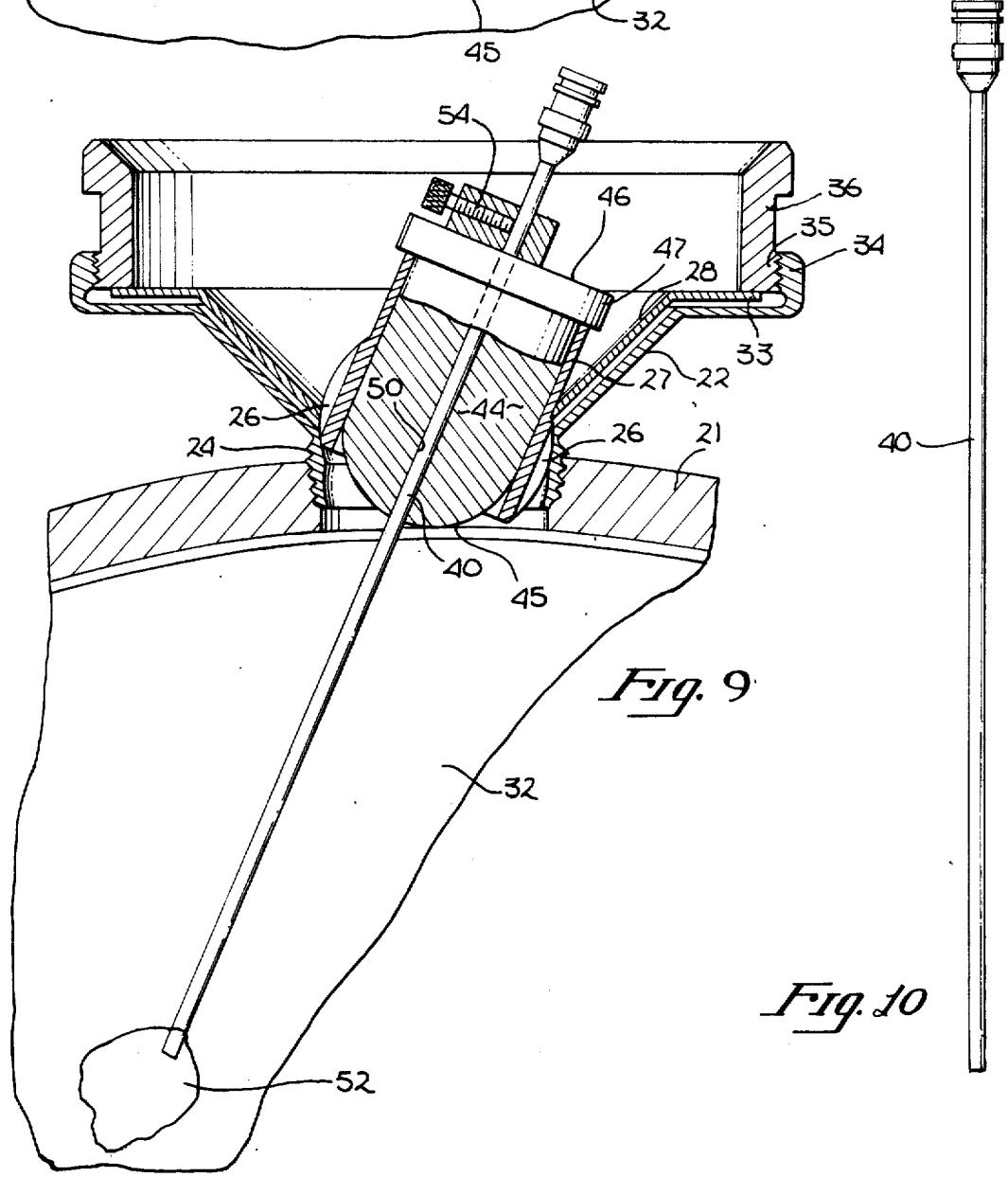
Fig. 9
Fig. 10

ULTRASOUND GUIDED SURGICAL INSTRUMENT GUIDE AND METHOD

FIELD OF THE INVENTION

This invention relates to a device for guiding a surgical instrument to a predetermined area using ultrasound, and more particularly, to a stereotactic guide for obtaining brain biopsies.

BACKGROUND

In the sampling or treatment of body tissues, and particularly brain tissue, it is important to be able to identify areas of tissue which require such sampling or treatment and to guide a cannula or biopsy needle to such areas. Once the needle or cannula is properly in place, a biopsy sample can be removed or a particular agent can be injected to such area through the cannula.

The precise placement of the needle in the target area is a critical step for obtaining biopsy samples. To locate the target area, a surgeon must first locate the general area within the skull in which the target area is located. This has typically been done using X-ray photography, although most recently, the use of CT (computerized tomography) scanning and NMR (nuclear magnetic resonance) have become more commonly used. However, CT scanners and, to a much greater extent, NMR machines, are considerably more expensive and less available than ultrasound and X-ray equipment, and require greater amounts of dedicated space.

The most common technique currently in use by neurosurgeons for locating lesions in the brain comprises fitting a circular crown containing precisely located pieces of radioactive material to the head of an individual and taking X-rays of the patient's head from various angles. Thereafter, the X-rays are examined using various trigonometric functions and the location of the lesions to be biopsied is determined. Similar techniques are utilized for CT scan detection of lesions.

Once the lesion is precisely located, the surgeon must then drill through the skull in the general area in which the lesion is located and take a biopsy of the tissue in that area. To take the biopsy, a biopsy needle is guided to the target area by means of a biopsy needle guide. Various such guides have been described in the prior art.

U.S. Pat. No. 3,021,842 issued to Flood discloses a device including a mounting plate that mounts to the surface of the skull or other bone tissue, and a spherical guide and a pair of locking rings for securing the spherical guide in said mounting plate. The spherical guide has a hole extending therethrough which can accommodate a needle.

U.S. Pat. No. 3,017,887 issued to Heyer discloses a brain surgery instrument for use in injecting various agents into the brain comprising a base that clamps to the skull, a ball disposed within a retaining ring in the base and a tube disposed through the ball from outside the skull to inside the brain. The tube can pivot but only a minimal amount. A protractor is provided to define the angle of the tube with respect to the skull.

U.S. Pat. Nos. 3,135,263 and 3,460,537 describe similar surgical instrument guides for use in positioning needles and the like in the brain.

All of the foregoing devices are designed to be used after the precise target area is identified using X-ray photography to identify the exact position of the lesion or other target area, and none can be used with ultrasound imaging to quickly, conveniently and precisely identify the target area and guide a biopsy needle or other instrument to the target area. Moreover, most of the foregoing devices have a very limited range of motion. Further, the devices generally require the taking of X-ray photographs while the biopsy or other instrumentation is disposed within the brain to be certain that the target area is reached by such instrumentation before the biopsy sample is obtained or any other treatment is performed on the brain tissue. The foregoing limitations of the prior art devices are overcome by the present invention, and other new and novel features of the present invention are described herein.

BRIEF SUMMARY OF THE INVENTION

The present invention utilizes ultrasound imaging to determine and guide the proper placement of a surgical instrument into the brain or other tissue. The invention comprises a mounting assembly that may be screwed into a burr hole in a patient's skull. A swivel ball disposed in the assembly, and a locking ring disposed over the swivel ball, which locking ring can be reversibly tightened to fix the swivel ball in place or loosened to allow it to swivel.

The swivel ball is formed to accommodate an ultrasound probe, and in particular, a small intra-operative probe. The swivel ball is slotted to permit liquid to freely flow from the interior to the exterior thereof, thereby preventing excessive fluid pressure on the brain when the probe is inserted into the swivel ball. In use, the probe is connected to an ultrasound image processor preferably with the capability of designating the center of the image field, and determining the depth of any particular location within said field. The invention further comprises a needle holder having a shape similar to that of the tip of the ultrasound probe, which can be disposed in the swivel ball. The needle holder has a centrally located hole through its axis, and can snuggly accommodate the needle or other instrument to be positioned in the target area.

To perform surgical instrument placement using the present invention, the general area of the brain lesion is identified using X-ray photography, CT scanning NMR, or the general target area is otherwise determined by means known in the art. A burr hole is then drilled in the skull or other area close to said general area. The mounting assembly is attached to a surface area close to target area by screwing it into the skull thereby securing it thereto. A locking ring is loosened to permit the swivel ball to rotate within its socket. The small diameter ultrasound probe is installed in the swivel ball. Due to the slots in the swivel ball, saline, or other liquid disposed in the hole for the purpose of maintaining a complete fluid pathway from the probe to the brain can be displaced when the probe is inserted without causing any undue pressure on the brain. The target area is then located using the ultrasound probe by pivoting the probe in the swivel ball until the lesion is positioned within the center of the image field. The depth of the lesion is also determined from the ultrasound image. The swivel ball is then locked in place and the probe removed therefrom, and replaced by the needle guide. The biopsy needle or other surgical instrument is disposed through the needle guide to the depth determined using the ultrasound imaging system so that the tip or other operative portion thereof is disposed within the target area, and the tissue at said tip is sampled or otherwise treated. The needle is properly disposed in the target area because the central axis of the needle guide is aligned with the center of the image field. Therefore, the insertion of the needle through the guide to the predetermined depth accurately locates the needle as desired.

BRIEF DESCRIPTION OF THE DRAWINGS

FIG. 1 is an illustration of the drilling of a burr hole in the skull.

FIG. 2 is an illustration of the further drilling of a sizing hole in the skull.

FIG. 3 is a side view of the present invention installed in the skull.

FIG. 6 is a sectional side view of the present invention with an ultrasound probe disposed therein.

FIG. 7 is an illustration of an ultrasound image showing the location of a lesion.

FIG. 8 is a sectional view of the present invention with the needle guide disposed in the swivel ball.

FIG. 9 illustrates the present invention with a needle disposed in the needle guide.

FIG. 10 illustrates a biopsy needle for use with the present invention.

DETAILED DESCRIPTION

Figure 4:
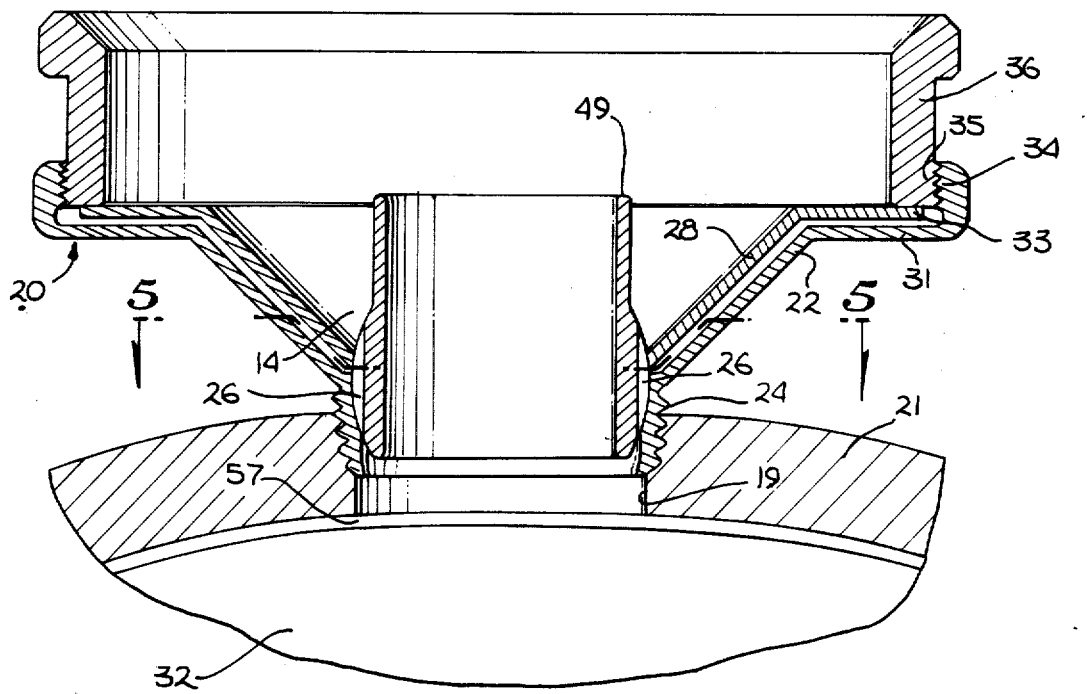
FIG. 4 is a sectional side view of the present invention taken through lines 4—4 of FIG. 3.
Figure 5:
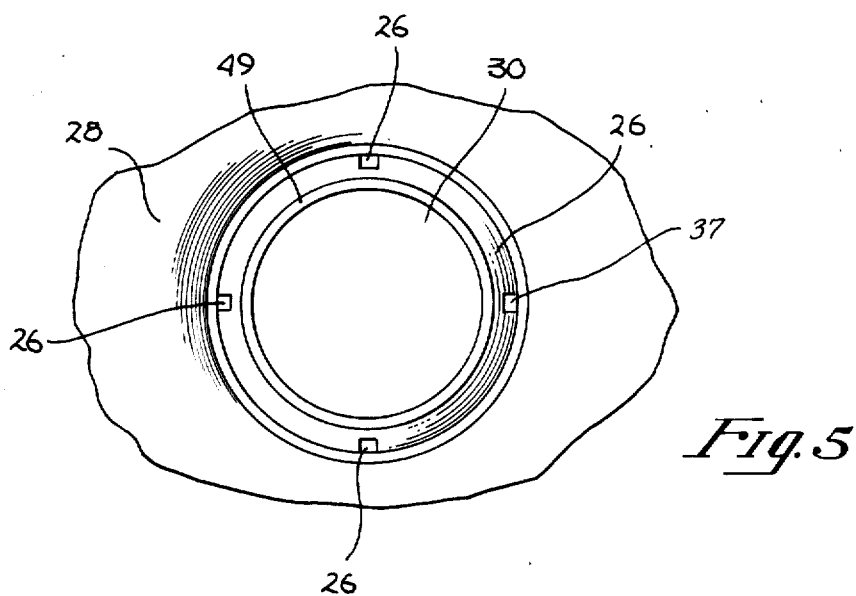
FIG. 5 is a sectional top view of the present invention taken through lines 5—5 of FIG. 4 illustrating the slots in the swivel ball.

The present invention is designed for use in a variety of surgical procedures whereby the placement of a surgical instrument in a specified target area identifiable using ultrasound is desired. Such procedures include obtaining biopsies of tissue, electrically stimulating target areas of brain, muscle, nerves, and the like, and delivering pharmaceutical agents to such target areas. Target areas identifiable using ultrasound imaging include most areas of the body in which the density of the tissue is substantially greater or lesser than the surrounding tissue. Examples of such identifiable target areas include lesions, such as tumors, stones, cysts, abcesses, blood vessels, heart valves and transitions between different types of material (i.e. muscle and bone, tissue and fluid).

The present invention is a stereotactic instrument guide for use in conjunction with a small access ultrasound probe designed for intra-operative procedures. The invention shall be generally described for use with a biopsy needle for locating and obtaining biopsy samples. However, it will be recognized by one skilled in the art, that the present invention can similarly be used to place catheters, electric probes and conductors, hypodermic needles and the like in target areas.

The preferred ultrasound system is the Diasonics Small Access Probe used with the Diasonics SurgiVue Imaging System (from Diasonics, Inc., Milpitas, Calif. The probe can be any size compatible with reasonable surgical technique regarding the size and shape of the hole made in bone tissue to provide access to the underlying tissue in which the target area is located. The preferred probe are a 5.0 MHz or 7.5 MHz burr hole neuro probe.

The invented needle guide comprises a mounting means for securing the needle guide in a fixed position in relation to a portion of the body near the target area. Referring first to FIG. 3, the preferred device for use in performing brain biopsies comprises an adaptor housing 22 with external self-tapping threads 24 for screwing the housing 22 into the skull 21. The adaptor housing 22 preferably has a roughened upper outer surface 23 to facilitate its gripping and handling. Disposed inside the adaptor housing 22 is a probe socket 14 comprising a swivel ball 26 formed with a hole 61 in the bottom thereof to permit an ultrasound probe 30 or needle 40 access to the underlying brain tissue 32, and a neck 27, formed to accommodate the shape of a typical intraoperate probe.

The swivel ball 26 has a rounded exterior that fits snuggly within the inside diameter of the adaptor housing 22 so that it can rotate therein. Optimally, the swivel ball can pivot a large angle from the vertical position and a sweep of 60 degrees (30 degrees from vertical in every direction) has been found to be effective.

The swivel ball 26 is of a sufficiently large diameter that it cannot fit through the bottom 61 of the adaptor housing 22. A clamp plate 28 having a hole in the center thereof with a diameter less than the diameter of the swivel ball 26 is disposed thereabove. The clamp plate 28 and adaptor housing 22 have parallel flanges 33 and 31 respectively such that downward pressure on the base clamp flange 33 squeezes swivel ball 26 against the inside surface of the adaptor housing 22 thereby locking it in place. A locking ring 36 disposed over base clamp flange 33 with threads 35 which mate with threads 34 on the base plate 22 can be screwed downward to force clamp plate 28 against swivel ball 26 thereby locking it in place. If the locking ring 36 is loose, probe socket 14 can freely rotate within adaptor housing 22.

As shown in FIG. 6, the inside of probe socket 26 is formed to receive an intra-operative ultrasound probe 30. The tip 41 if the probe is approximately the length of the probe socket 14 so that the probe tip 41 fits securely therein without any risk of it sliding downward into the brain tissue 32. It is important that the probe 30 is as close to the brain as possible because the entire gap between the probe 30 and brain tissue 32 must be filled with gel or liquid, such as saline, otherwise, any bubbles or gaps therebetween reflect the ultrasound waves thereby decreasing the resolution of the system. To prevent any excess pressure build-up inside the swivel ball 26 when the probe 30 or needle guide 44 are inserted therein, thereby displaying saline or gel disposed in the probe socket 14, slots 37 are disposed in the swivel ball 26 to allow said aline or gel to exit and enter the swivel ball 26. In use, it is common surgical technique to cover the probe with sterile dressing to prevent contamination of the exposed body tissue.

The probe 30 is not locked into the swivel ball 26 so that it can be removed easily and replaced with the needle guide 44. The needle guide 44 has an exterior shape and size similar to the tip 41 of the probe 30, and is generally cylindrical with a rounded proximal tip 45 and a hole 50 through its center. At the distal end 46 is a lip 47 which catches the top 49 of the swivel ball 26 so that the needle guide 44 is secured in position.

As shown in FIG. 10, a biopsy needle 40 or any other extended surgical tool can be disposed through the hole 50 in the needle guide 44 to permit access to the brain tissue 32, generally, and specifically, the lesion or other target area 52. A needle stop 54 may be disposed on said needle to mark the desired depth to which the needle 40 is intended to go.

METHOD OF USE

The present invention can best be understood with reference to the method of using said invention to obtain a biopsy of tissue from a target area in the brain. To obtain a biopsy, the general area of the skull close to the target area is first identified preferably using X-ray photography, although CT scanning or NMR scanning could provide the location as well. The exact location of the target need not be found using this method, but the target area should be within about 10 centimeters or less, and preferably within 6 centimeters, and within 30 degrees from the vertical, in any direction of a burr hole to be made in the skull.

The following steps are performed using standard neurosurgical procedures regarding safety and sterility. First, an incision is made in the skin covering the skull over the target area. In the next step shown in FIG. 1, a burr hole 18 is started in the skull 21 using a drill. In standard neurosurgical practice, first a rounded hole 18 is drilled using a rounded bit 15 as shown in FIG. 1, and then the edges of the hole 19 are squared off using a sizing cutting drill bit 16, and finally the lip 17 of the remaining skull in the hole 19 may be removed using a rongeur (not shown), as one skilled in the art would recognize.

After the hole 19 is made, the invented ultrasound guided surgical instrument guide 20 is installed in the skull. The adaptor housing 22 is screwed into the skull 21 using the self-tapping threads 24 until the bottom 29 thereof is adjacent the dura 57, the tissue covering the brain. It is important for the housing to be reasonably close to the dura so that a complete liquid medium can be placed between an ultrasound probe and the brain tissue.

After adaptor housing is secured in the skull, the probe socket 14 is installed in the center thereof and the clamp ring 28 is disposed thereover. The locking ring 36 is then screwed into the adapt or housing 22. So long as the locking ring 36 is loose, the probe socket 14 can rotate, so therefore, the locking ring 36 is kept loose at this stage. The probe socket is then filled with saline, gel or other sterile liquid which will conduct the ultrasound waves to be emitted and received by the probe. Any bubbles, gaps or pockets of air will reflect the ultrasound waves thereby creating artifacts on the image screen.

The probe 30 is then sterilely dressed and inserted into the probe socket 14 as shown in FIG. 6. Any excess fluid in the probe socket 14 will escape through slots 37 in the probe socket 14, as the probe 30 is inserted therein, and thus, excess pressure on the brain is avoided. The ultrasound imaging device is then activated and a display similar to that shown in FIG. 7 may be seen. FIG. 7 illustrates the image obtained from an arrangement as shown in FIG. 6. The target area 52 is located in the field of the image 59. As the probe is rotated to point toward the target area 52, the target area 52 moves closer to the hash market line 54, which appears in the middle of the field, so that the target area 52 is intersected by the line 54 in the center of the image 59. Using the SurgiVue system, a cursor 63 is placed on the target area 52 and data is provide by the system indicating the depth of the target area. If the SurgiVue system is not in use, other methods of depth calculations known in the art such as taking calibration measurements should be employed to determine the depth of the target area 52. At this stage, the longitudinal axis of the probe 30 is directly pointing at the target area 52. The locking ring 36 is then tightened to fix the probe socket 14 in place aimed at the target area 52.

The probe 30 is then removed from the probe socket 14 and replaced by the needle guide 44. A needle 40 or other device to be installed at the target area is set for the proper distance as determined above. A known distance must be added to the target area distance to account for the height of the needle guide 44, since the probe 30 measured distance from the tip thereof and as presently exemplified, the needle stop 54 is disposed above the needle guide 44. In the presently contemplated embodiment, the needle guide is approximately 3 centimeters long, so this constant should be added to the depth of the target area from the tip of the probe. The needle 40 is then disposed through hole 50 and will automatically be disposed at the target area so that the biopsy can be taken.

The entire foregoing procedure from the skin incision through the taking of the sample takes from 20 to 40 minutes for a skilled surgeon to perform, as compared with prior art methods taking 2 to 3 hours. This amount of time is a substantial consideration, since the longer an operation takes, the greater are the risks of infection.

It will be apparent to one of ordinary skill in the art that many modifications could be made to the present invention without departing from the nature and scope of the present invention. Moreover, the invention is not intended to be limited to the preferred embodiments described herein but is as broad as the scope of the claims appended hereto.

What is claimed is:

1. An ultrasound guided instrument guide comprising:

an adaptor housing having a central portion, said adaptor housing having a hole through said central portion thereof for providing access of an ultrasound probe disposed therein to a volume therebelow, said adaptor housing having a lower threaded portion for screwing said adaptor housing in a burr hole in a skull and an upper threaded portion;

a probe socket disposed in said hole in said adaptor housing, said probe socket with passage therethrough for holding an ultrasound probe by its tip portion, said probe socket comprising a spherical member and a neck member attached thereto;

a clamp ring disposed over said probe socket;

a locking ring disposed over said clamp ring, said locking ring being threaded to mate with said upper threaded portion of said adaptor housing such that the tightening of said lock ring with respect to said adaptor housing applies pressure to said clamp ring thereby locking said probe socket in position; and an instrument holder formed in the shape of said ultrasound probe tip and having a hole disposed through its longitudinal axis adapted to hold said instrument therein.

2. The instrument guide of claim 1 wherein said probe socket further comprises slots disposed therein for allowing fluid to flow from the inside to the outside thereof.

3. The instrument guide of claim 2 wherein said instrument guide is formed of a sterilizable, non-toxic material.

4. An ultrasound guided instrument guide comprising:

a substantially fruco-conical housing having a vertical wide upper portion and a vertical narrow lower portion, said lower portion having external self-tapping threads, and said upper portion having threads on the inner surface thereof;

a probe socket comprising a spherical lower portion of greater size than said narrow lower portion of said housing and a cylindrical upper portion, said probe socket having a cavity disposed therethrough for holding an ultrasound probe therein, and providing said probe with access to a tissue thereunder; said spherical portion having fluid communicating holes therein to permit passage of fluid between a outside and inside thereof;

a locking means for reversibly locking said socket in a fixed position with respect to said housing, said locking means comprising:

a clamp ring disposed over said spherical portion of said probe socket; and a locking ring disposed adjacent said clamp ring and threaded to mate with said upper portion of said housing such that the tightening of said locking ring applies pressure to said clamp ring, which, in turn, forces said spherical portion against said housing thereby locking it in place; and an instrument guide comprising a substantially cylindrical housing with a spherical lower end, a lip on the upper end thereof, and a hole through the central axis thereof for holding said instrument.

* * * * *

UNITED STATES PATENT AND TRADEMARK OFFICE
CERTIFICATE OF CORRECTION

PATENT NO. : 4,681,103

DATED : July 21, 1987

INVENTOR(S) : Boner et al.

It is certified that error appears in the above-identified patent and that said Letters Patent is hereby corrected as shown below:

| COLUMN | LINE | |
|---|---|---|
| 3 | 58 | insert -- ) -- after "Calif.". |
| 4 | 49 | delete "aline" and insert --saline--. |

Signed and Sealed this

Twenty-first Day of June, 1988

Attest:

DONALD J. QUIGG

*Attesting Officer*  *Commissioner of Patents and Trademarks*